(12) United States Patent
Varn

(10) Patent No.: US 6,773,410 B2
(45) Date of Patent: Aug. 10, 2004

(54) DORSAL CARPAL TUNNEL SPLINT

(76) Inventor: Harold T. Varn, 2335 Farm Bell La., Lawrenceville, GA (US) 30244

( * ) Notice: Subject to any disclaimer, the term of this patent is extended or adjusted under 35 U.S.C. 154(b) by 590 days.

(21) Appl. No.: 09/733,359

(22) Filed: Dec. 8, 2000

(65) Prior Publication Data

US 2002/0072696 A1 Jun. 13, 2002

(51) Int. Cl.[7] .................................................. A61F 5/00
(52) U.S. Cl. ............................... 602/13; 602/5; 602/20; 602/21; 602/22
(58) Field of Search ............................ 602/5–8, 20–22; 128/846, 877–879

(56) References Cited

U.S. PATENT DOCUMENTS

| | | | | |
|---|---|---|---|---|
| 5,205,812 A | * | 4/1993 | Wasserman | 602/5 |
| 5,358,471 A | * | 10/1994 | Klotz | 602/21 |
| 5,415,623 A | * | 5/1995 | Cherubini | 602/7 |
| D371,845 S | | 7/1996 | Varn | |
| 5,637,078 A | * | 6/1997 | Varn | 602/21 |
| 5,746,707 A | * | 5/1998 | Eck | 602/21 |
| 5,766,142 A | | 6/1998 | Hess | |
| 5,778,449 A | * | 7/1998 | Spaulding et al. | 2/16 |
| 6,120,471 A | | 9/2000 | Varn | |

* cited by examiner

Primary Examiner—Nicholas D. Lucchesi
Assistant Examiner—Lalita M Hamilton

(57) ABSTRACT

A dorsal carpal tunnel splint has an elongated stiff splint element having an upper end, a lower end and a center portion. The splint element is arcuate in cross section and has a length and lateral breadth sufficient to engage the outer surface of the lower forearm, the wrist, and the hand of the wearer. First straps are secured to the upper end and the center portion of the splint for securing the splint to the patient's forearm and wrist. A finger strap extends along the lower end of the splint and forms a loop thereunder to receive the fingers only of the wearer's hand and to provide a space for the wearer's thumb outside the loop. A resilient liner pad is secured to an inner surface of the splint element.

10 Claims, 5 Drawing Sheets

DORSAL CARPAL TUNNEL SPLINT

BACKGROUND OF THE INVENTION

Carpal Tunnel Syndrome (CTS) is defined as compression of the median nerve as it passes through the anatomical structures that form the carpal tunnel of the wrist.

CTS may be caused by any activity or condition resulting in a mechanical alteration of the carpal tunnel. This may be caused by repetitive activities of the wrist and arms. The change in orientation of the carpal tunnel may result in interference with the soft tissue structures within, most notably the median nerve. The carpal median nerve and nine tendons that pass from the forearm to the hand. The strength and stability of that passageway is maintained by bone structure and ligament integrity, as there are no muscles in the wrist. Repetitive use of the wrist during the course of the day naturally promotes laxity of the supportive ligaments, causing the compensating muscles to stabilize, the vulnerable carpal tunnel configuration will be altered. The proper juxtaposition of the radius and ulna is contingent upon a stable interosseous ligament. Separations of the radius and ulna from the middling will result in a migration of the lunate bone to the volar surface, protruding into the carpal tunnel itself and diminishing the available space within. This results in a structural alteration that is a decrease on flattening of the normally deep "u" shape of the carpal tunnel.

This distortion of the carpal tunnel, when present over an extended period of time will cause compression, irritation and inflammation of the soft tissue structures within, especially the median nerve, the subsequent symptoms of CTS directly related to the use of the wrist after the presence of this functions disrelationship.

The medical treatment of CTS usually begins with an immobilization splint. This splint might be used throughout the day or at night only. Upon this initial treatment protocol failing, a more aggressive approach might be taken. Physical Therapy in conjunction with flexibility exercise might then be used. More extreme forms of treatment include steroid injections and surgery to release the transverse ligaments, however the complications and instabilities that may result should place these treatments as a last resort. Common alternative approaches to traditional treatments might include chiropractic, acupuncture, nutritions, counseling, homeopathy and ergonomic recommendations. If a patient's condition is allowed to progress to the state of diseased tissue, conservative care may then be futile.

When inflammation is severe, immobilization may have limited short-term benefits. However, maintaining lack of motion is counter productive. Current management of soft tissue injuries advocates the rapid initiation of passive movement to prevent the development of adhesions and ultimately permanent scar formation.

Prior art devices do not incorporate concepts of tissue rehabilitation. Devices with elastic straps should be avoided because they compress the radius and ulna together, limiting proper translation upon flexion and extension, and expand the anterior to posterior dimension of the wrist by increasing inter-tunnel pressure. The median nerve is thereby further compressed, additionally, the Vernon forces of the elastic wrist splints are 360 degrees, directly pressuring the already protruding open anterior portion, worsening the symptoms the longer they are used. One big problem with volar designs is that hard material, such as a metal spoon or support, leather, vinyl or canvases make functional use of the hand difficult. One problem in this day and age is computer use. While using a computer one has to use their wrist and fingers, and the hand motion mentioned above would interfere or hinder the use of the wrist and fingers.

It is therefore a principal object of this invention to provide a dorsal carpal tunnel splint which limits wrist flexion and extension during repetitive hand motion.

A further object of the invention is to provide a dorsal design that frees the volar side of any hard material, which would interfere with everyday uses of the hand and which frees the volar side and does not interfere with the wrist and fingers.

A still further object of the invention is to provide a dorsal carpal tunnel splint which will permit the wearer to use their fingers for everyday activities such as writing, typing, driving and grasping, and which can be worn during any repetitive work without injury.

A still further object of the invention is to provide a dorsal carpal tunnel splint which allows the clinician to change the angle of the splint at the wrist to limit flexion or extension.

These and other objects will be apparent to those skilled in the art.

SUMMARY OF THE INVENTION

A dorsal carpal tunnel splint has an elongated stiff splint element having an upper end, a lower end and a center portion. The splint element is arcuate in cross section and has a length and lateral breadth sufficient to engage the outer surface of the lower forearm, the wrist, and the hand of the wearer. First straps are secured to the upper end and the center portion of the splint for securing the splint to the patient's forearm and wrist. A finger strap extends along the lower end of the splint and forms a loop thereunder to receive the fingers only of the wearer's hand and to provide a space for the wearer's thumb outside the loop. A resilient liner pad is secured to an inner surface of the splint element.

DESCRIPTION OF THE PREFERRED EMBODIMENT

Figure 1:
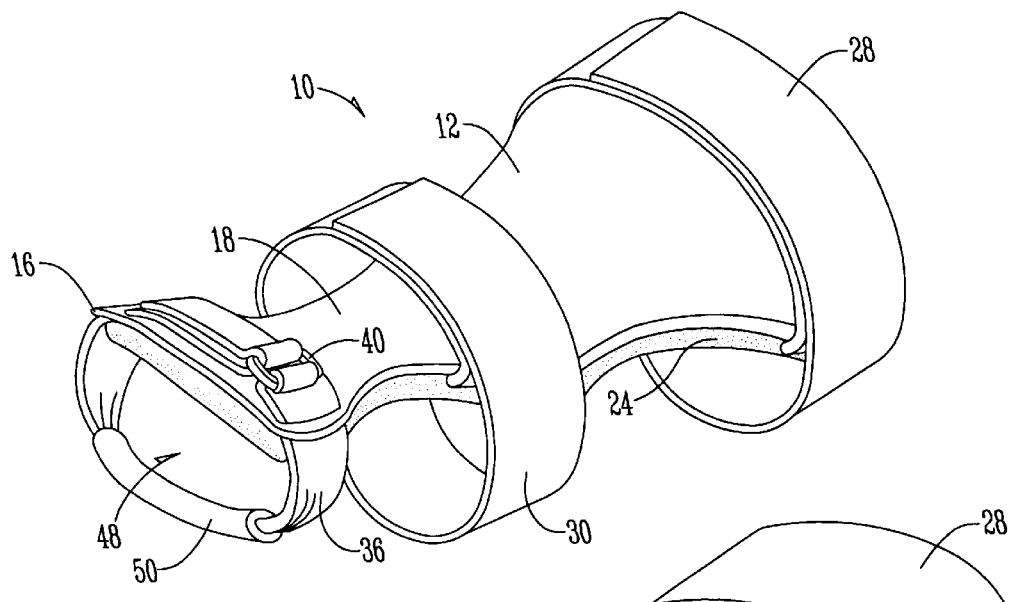
FIG. 1 is a perspective view of the top of the device of this invention.

With reference to FIGS. 1–8, the splint 10 of this invention includes an elongated stiff splint element 12 having an upper end 14, a lower end 16 and a center portion 18. The splint element 12 is comprised of a moldable Kydex® thermoplastic which allows the clinician to change the angle of the splint from time to time to accommodate the particular wrist configuration and working situation of the patient wearing the splint. By heating the splint element 12, for example, the angle between the lower end 16 can be changed with respect to the center portion 18. The splint has an outer surface 20 and an inner surface 22. A resilient liner pad 24 is detachably secured to the inner surface 22 of splint 12 by means of hook retainer strips 26 which conventionally adhere to the "loop" structure of the resilient liner pad 24.

A strap 28 extends around the upper end 14 of splint element 12. Similarly, a strap 30 is detachably secured to and extends around the center portion 18 of the splint 12. The straps 28 and 30 are detachably held in place through the conventional connection means of hook retainer strips 32 on the back of splint 12.

Similarly, hook retainer strips 34 are mounted on the straps to facilitate the free end of the strap being bent over and secured against the upstream portion of the strap when mounted on the forearm of a patient.

A finger strap 36 having a first end 38 with a buckle 40 thereon, and a second end 42 with a hook retaining strip 44 thereon (FIG. 6) is threaded through slots 46 in splint 12 to create loop portion 48. A hollow resilient tubular finger pad 50 is threaded on the loop portion 48 to provide finger support as will be explained hereafter.

Figure 2:
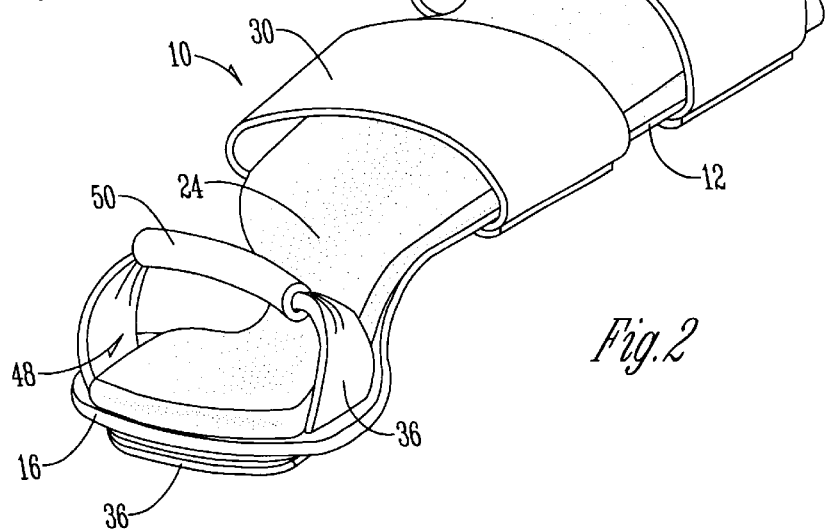
FIG. 2 is a perspective view of the bottom of the device of this invention.
Figure 3:
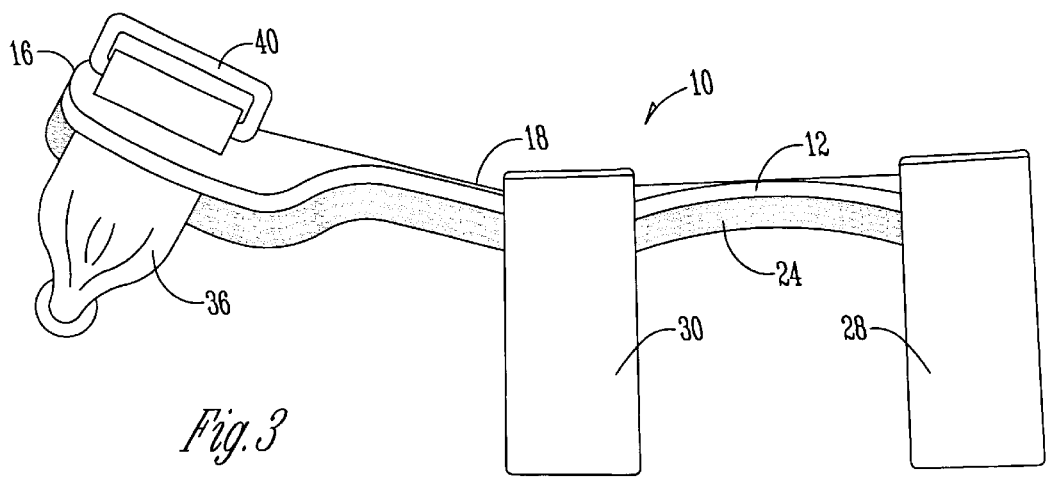
FIG. 3 is a side elevational view of the device shown in FIG. 1.
Figure 4:
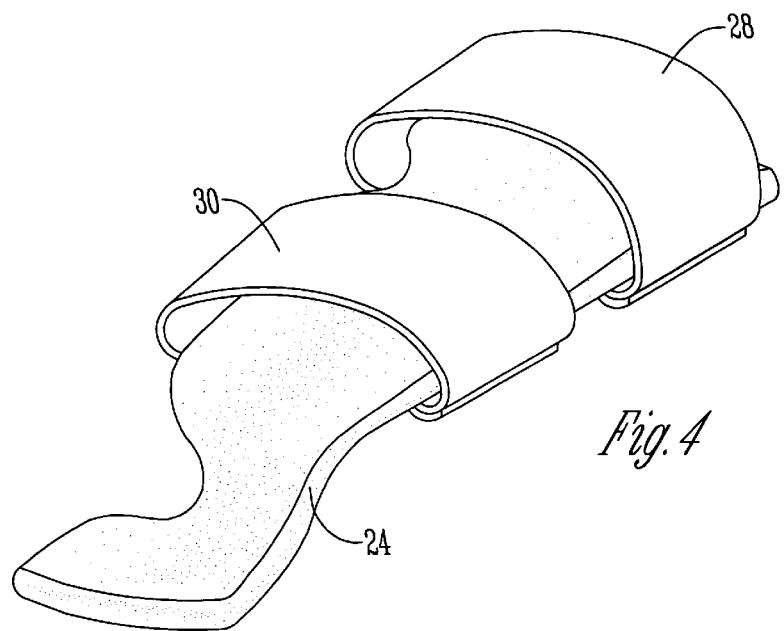
FIG. 4 is a bottom plan view of a resilient liner pad with attached straps.
Figure 5:
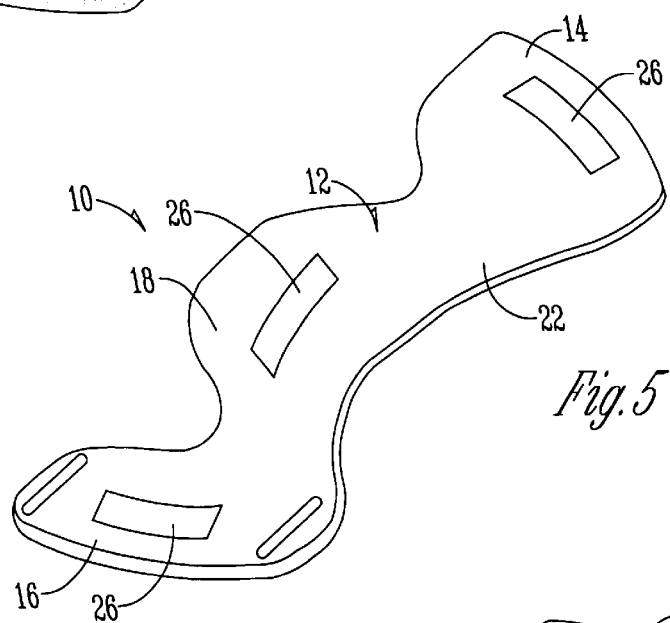
FIG. 5 is a bottom perspective view of the splint element.
Figure 6:
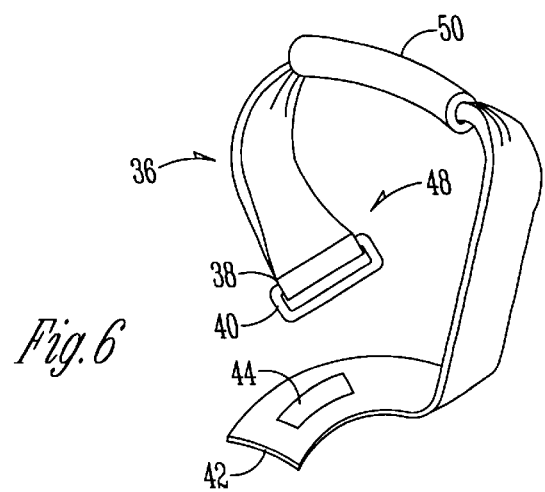
FIG. 6 is a perspective view of the finger strap.
Figure 7:
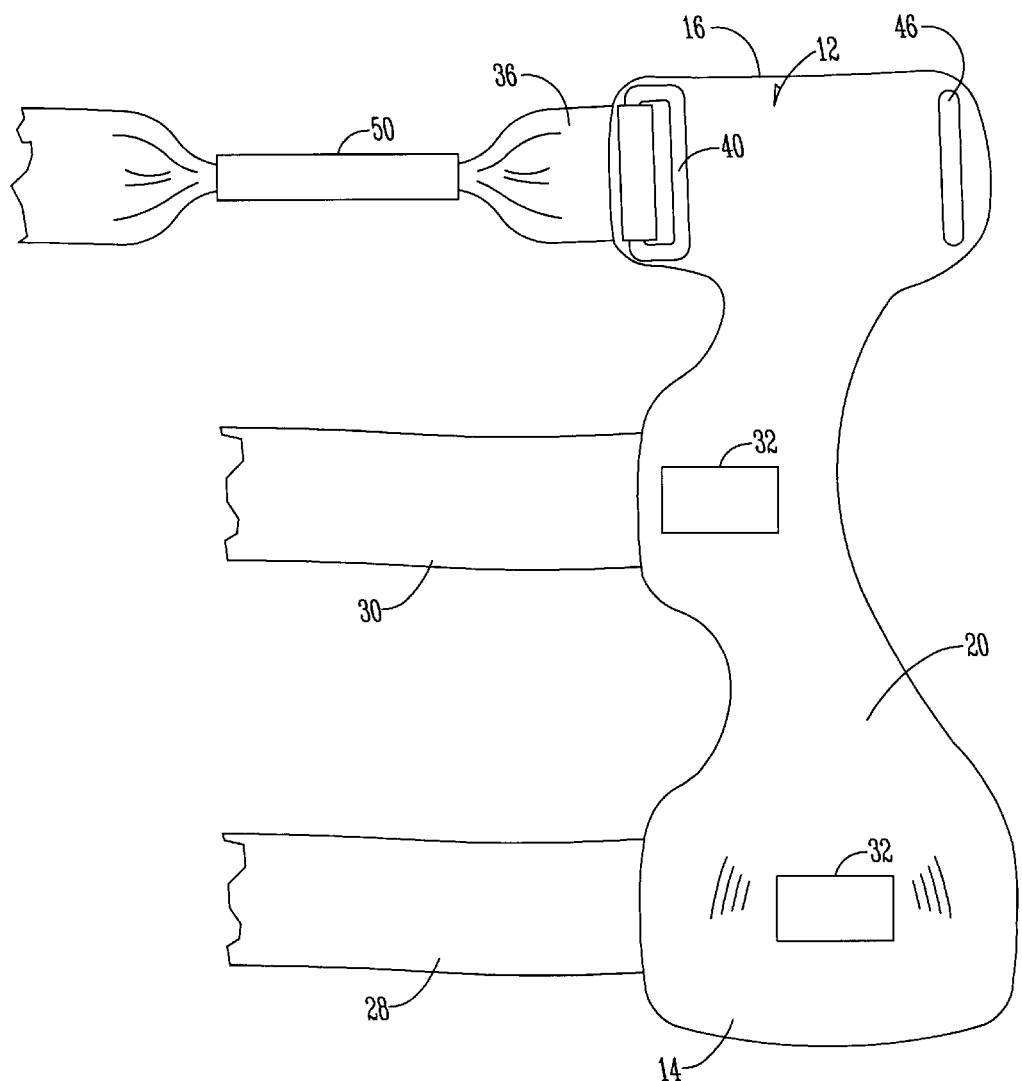
FIG. 7 is a plan view of the top of the splint element.
Figure 8:
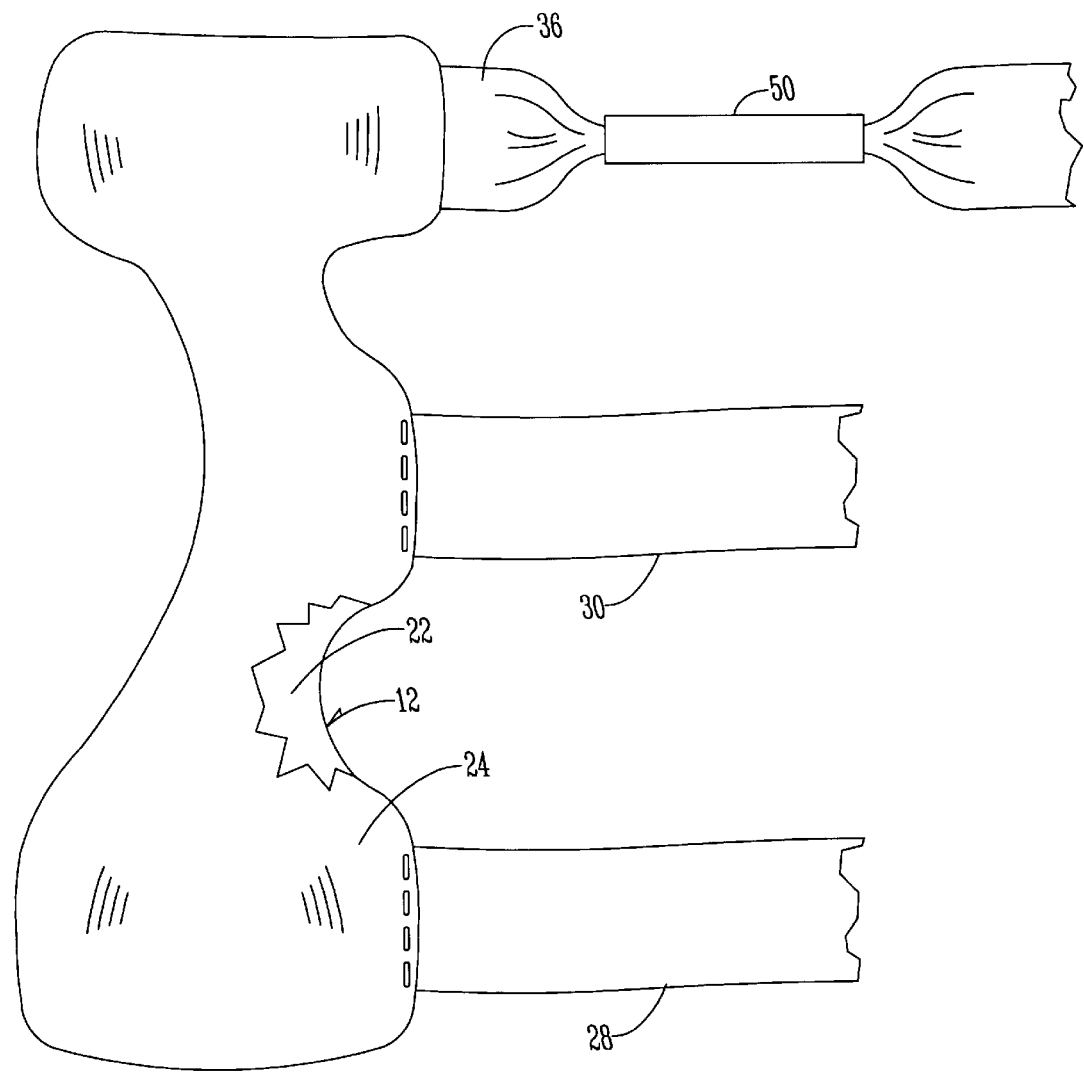
FIG. 8 is a bottom plan view of the splint with the resilient liner pad attached.
Figure 9:
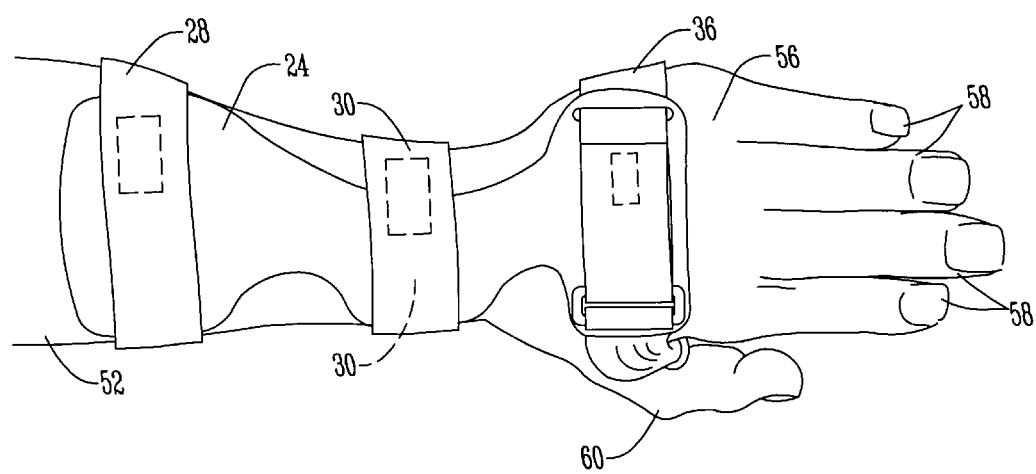
FIG. 9 is a plan view of the splint attached to the forearm of a patient.
Figure 10:
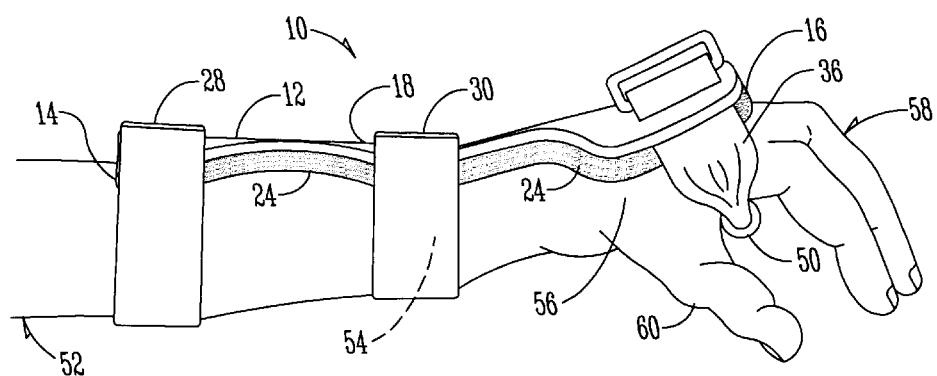
FIG. 10 is a side elevational view of FIG. 9.

With reference to FIGS. 9 and 10, the numeral 52 designates the lower forearm of the patient having a wrist 54, hand 56, fingers 58 and thumb 60. The splint 10 is assembled as generally indicated in FIGS. 1 through 3 and is placed on the dorsal or upper surface of the forearm, wrist and hand of the patient as indicated in FIG. 10. The fingers 58 of the patient extend through the loop portion 48 of finger strap 36 and are nested over the hollow resilient tubular finger pad 50. The splint 10 is held in place on the patient's forearm, wrist and hand by the straps 28, 30 and 36. The straps 28 and 30 are wrapped around the forearm 52 and wrist 54, respectively, and are held in place by the contact between the loop material of the straps becoming engaged with the hook strips 26 on the splint element 12. Overlapping ends of the straps 28 and 30 can be held in engagement with the main body of the straps by use of the conventional hook retainer strips 34 engaging the material of the straps.

Similarly, the finger strap 36 is stabilized with respect to the splint by threading the end 42 thereof through the buckle 40 in conventional fashion and securing the same in place by causing the hook strip 44 to overlap and engage the strap itself. As previously indicated, with reference to FIG. 3, the end 16 of the splint element 12 can be altered with respect to the center portion 18, for example, by heating the center portion 18 and bending the splint element 12 to the desired angle between the end 16 and the center portion 18. This could be done to accommodate a given patient's condition or the working situation in which the patient is involved.

The splint 10 of this invention limits wrist flexion and extension during repetitive hand motion. By placing the splint 10 on the dorsal side of the patient's arm, wrist and hand, the palm portion and fingers of the hand are freed for everyday uses of the hand. This is in contrast with prior art devices wherein the palm is inhibited with hard material such as a metal spoon or support, leather, vinyl or canvasses which make functional use of the hand difficult. This is particularly true of conventional use of modern computers. While using a computer, one has to use their wrist and fingers and hard material in the area of the palm would interfere or hinder the use of the wrist and fingers. Again, by locating the splint 12 on the dorsal side of the forearm, wrist and hand, the palm side is free for movement and nothing there interferes with the wrist and fingers. Thus, the wearer is free to use their fingers or hand in everyday activities, such as writing, typing, driving and grasping objects.

The splint 10 of this invention is very comfortable to wear sleeping because the dorsal design does not put any pressure on the conventional incision site if the patient is wearing the splint after carpal tunnel surgery. The splint 10 can be worn during any repetitive work related activity to prevent injury. It helps to prevent damaging wrist flexion, and restores finger sensation and improves hand strength for the patient with carpal tunnel syndrome. The breathable resilient liner pad 24 made of Orthowick® material absorbs perspiration and moisture and is replaceable and washable along with the straps attached thereto. The hollow resilient tubular finger pad 50 serves as a roll on finger strap 36 to allow free movement of the fingers so that the patient can perform virtually all hand and finger functions.

It is therefore seen that this invention will achieve at least all of its stated objectives.

What is claimed is:

1. A dorsal carpal tunnel splint, comprising, an elongated stiff splint element having an upper end, a lower end, and a center portion that respectively define an upper end, a lower end, and a center portion of the splint, the splint element being arcuate in a lateral cross section and having an unbroken length and lateral breadth sufficient to engage a major portion of the dorsal outer surfaces of the lower forearm, the wrist, and the hand of the wearer, by the upper end, the center portion, and the lower end of the splint element, respectively, first and second straps secured to the upper end and center portion of the splint for securing the splint to the lower forearm and wrist of the wearer, respectively, a finger strap extending from the lower end of the splint element and forming a loop thereunder to receive the fingers only of the wearer's hand and to provide space for the wearer's thumb outside the loop, and means for detachably securing the finger strap to the lower end of the splint element.

2. The splint of claim 1 wherein the splint element has an inner surface, a resilient liner pad detachably mounted on the inner surface to provide a cushion between the splint element and the lower forearm, wrist, and hand of the wearer.

3. The splint of claim 2 wherein the liner pad is of a material that it will absorb perspiration of the wearer.

4. The splint of claim 2 wherein the first and second straps are secured to the liner pad.

5. The splint of claim 4 wherein the finger strap is secured to the lower end of the splint element and not the liner pad.

6. The splint of claim 5 wherein the first and second straps are permanently attached to the liner pad and are thereby detachably removable as a single unit therewith from the splint element for cleaning.

7. The splint of claim 5 wherein the lower end of the splint element has a pair of elongated laterally spaced slots therethrough that slidably receive the finger strap and the finger strap has a buckle thereon located between the slots and adjacent an outer surface of the lower end of the splint element.

8. The splint of claim 1 comprising a tubular resilient roll that surrounds a lower portion of the loop.

9. The splint of claim 1 wherein the material of the splint element is a heat moldable thermoplastic so that the configuration of the splint can be changed to accommodate special circumstances of a wearer's carpal tunnel condition or working situation.

10. A dorsal carpal tunnel splint, comprising, an elongated stiff splint element having an upper end, a lower end, and a center portion that respectively define an upper end, a lower end, and a center portion of the splint, the splint element being arcuate in a lateral cross section and having a length and lateral breadth sufficient to engage the dorsal outer surfaces of the lower forearm, the wrist, and the hand of the wearer, by the upper end, the center portion, and the lower end of the splint element, respectively, first and second straps secured to the upper end and center portion of the splint for securing the splint to the lower forearm and wrist of the wearer, respectively, a finger strap extending from the lower end of the splint element and forming a loop thereunder to receive the fingers only of the wearer's hand and to provide space for the wearer's thumb outside the loop, a tubular resilient roll surrounding a lower portion of the loop, and means for detachably securing the finger strap to the lower end of the splint element.

\* \* \* \* \*